US007208508B2

(12) United States Patent
Daemmgen et al.

(10) Patent No.: US 7,208,508 B2
(45) Date of Patent: Apr. 24, 2007

(54) USE OF BRADYCARDIAC SUBSTANCES IN THE TREATMENT OF MYOCARDIAL DISEASES ASSOCIATED WITH HYPERTROPHY AND NOVEL MEDICAMENT COMBINATIONS

(75) Inventors: Juergen Daemmgen, Ochsenhausen (DE); Brian Guth, Warthausen (DE); Randolph Seidler, Mittelbiberach (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 10/257,481

(22) PCT Filed: Apr. 7, 2001

(86) PCT No.: PCT/EP01/04034

§ 371 (c)(1),
(2), (4) Date: Jun. 13, 2003

(87) PCT Pub. No.: WO01/78699

PCT Pub. Date: Oct. 25, 2001

(65) Prior Publication Data

US 2004/0014795 A1    Jan. 22, 2004

(30) Foreign Application Priority Data

Apr. 13, 2000  (DE) ................. 100 18 401

(51) Int. Cl.
*A61K 31/455* (2006.01)
(52) U.S. Cl. .................................. 514/355
(58) Field of Classification Search ................ 514/355
See application file for complete search history.

(56) References Cited

U.S. PATENT DOCUMENTS

| 5,175,157 | A |   | 12/1992 | Psiorz et al. |
| 5,308,853 | A | * | 5/1994  | Hodges et al. ............ 514/336 |
| 5,516,773 | A |   | 5/1996  | Rose |
| 5,595,987 | A | * | 1/1997  | Lasker et al. .......... 514/213.01 |
| 5,721,217 | A |   | 2/1998  | Liu et al. |
| 5,968,978 | A |   | 10/1999 | Kleemann et al. |
| 6,083,991 | A | * | 7/2000  | Bergeron, Jr. ............ 514/646 |
| 2004/0138306 | A1 |   | 7/2004 | Guth et al. |

FOREIGN PATENT DOCUMENTS

| CA | 2435526 | 1/2004 |
| DE | 3541811 | * 6/1987 |
| EP | 0 224 794 | 6/1987 |
| EP | 0330052 | 8/1989 |
| EP | 0 471 388 | 2/1992 |
| WO | WO 00/02543 | 1/2000 |
| WO | WO 01/78699 | 4/2001 |
| WO | WO 0178699 | 10/2001 |

OTHER PUBLICATIONS

Toshiima et al "Comparable effects of oral dilitazem and verapamil in the treatment of hypertrophic cardiomyopathy", Japanese Heart Journal, Bd. 27, Nr. 5, 1986, 701-715.*
Merck Index, 12th Ed., 1996, pp. 541 and 1696.*
The Merck Manual, 15th Edition, 1987, pp. 519-522.*
Rieu et al, Eur. J. Med. Chem. 1993, 28, 683-691.*
Goodman & Gilman's: The Pharmacological Basis of Therapeutics, 10th Edition, McGraw-Hill Medical Publishing Division, 2001, pp. 54-56.*
P. Gregor, et al; Use of Verapamil in the Treatment of Hypertrophic Cardiomyopathy, Cor Et Vasa, Bd. 28 Nr. 6, 1986, pp. 404-412, XP 001024692.
A. Hartmann, et al; Persisting effect of Calcium-channel blockers on the left ventricular function in hypertrophic cardiomyopathy after 14 years' treatment, Angiology, Bd. 47, Nr. 8, 1996 pp. 765-773- XP 00124817.
H. Toshima, et al; Comparable effects of oral diltiazem and verapamil in the treatment of hypertrophic cardiomyopathy, Japanese Heart Journal, Bd. 27, Nr. 5, 1986 pp. 701-715, XP0010214687.
G. Kober, et al; Clinical cardiology hypertrophic cardiomyopathy. Long-term verapamil versus propranolol treatment of hypertrophic cardiomyopathy in matched pairs of patients, Circulation Supplement, Abstracts from the 60th Scientific Session Bd. 76, Nr. 4, 1987 p. IV-248-XP001024696.
S.E. Epstein, et al; Verapamil; Its potential for causing serious complications in patients with hypertrophic cardiomyopathy; Circulation, Bd. 64, Nr. 3, 1981, pp. 437-441 XP001024694.
Database WPI, Section PQ, Week 199747 Derwent Publications Ltd. London, GB; Class P31; AN 1997-510672, XP 002179143.
The Extra Pharmacopoeia, 30th Edition, The Pharmaceutical Press, London, XP 002179142, p. 668.
T. Shinke, et al; Beneficial effects of heart rate reduction on cardiac mechanics and energetics in patients with left ventricular dysfunction, Japanese Circulation Journal, English Edition, vol. 63, No. 12 pp. 957-964.
J.P. Rieu, et al; Synthesis and bradycardia activity of a series of substituted 3-aminoalkyl-2,3-dihydro-4H-1,3-benzoxazin-4-ones as potent antiischemics, Europena Journal of Medicinal Chemistry, vol. 28, No. 9, pp. 683-691.

(Continued)

*Primary Examiner*—Shaojia Anna Jiang
*Assistant Examiner*—Ganapathy Krishnan
(74) *Attorney, Agent, or Firm*—Michael Morris; Mary-Ellen M. Devlin; Thomas Blankinship

(57) ABSTRACT

The present invention relates to the new use of bradycardiac substances such as a $Ca^{++}$ channel blocker, beta-receptor blocker or $i_f$ channel blocker, the $i_f$ channel blockers being preferred, optionally in combination with a cardioactive substance for inducing the regression of myocardial diseases accompanied by hypertrophy, particularly for the treatment of idiopathic hypertrophic cardiomyopathies (HCM) in humans and domestic pets.

1 Claim, No Drawings

OTHER PUBLICATIONS

D.P. Nichols, et al; Cardio Vascular effects of Alinidine and Propranolol alone and in combination with Hydralazine in Normal Man, Br. J. Clin. Pharmacol, (1983) 15 (1), 21-30-XP001041903.
International Search Report Dec. 13, 2001.
Muller, C. A. et al.; Combination of a Calcium Antagonist, Verapamil, with an Angiotensin Converting Enzyme Inhibitor, Trandolapril, in Experimental Myocardial Ischemia and Reporfusion; Antiarrhythmic and Hermodynamic Effects of Chronic Oral Pretreatment); Cardiovascular Drugs and Therapy 1998; 12:449-455;Kluwer Academic Publishers, Boston.
Ruschitzka, F.T., et. al.: Combination of ACE Inhibitors and Calcium Antagonists: A logical approach;J Cardiovasc Pharmacol, vol. 31 Supplement 2, 1998, pp. S5-S16.
The Merck Manual, 1987, 15th Edition, pp. 519-522.
Goodman & Gilman's: The Pharmacological Basis of Therapeutics, 10th Edition, McGraw-Hill Medical Publishing Division, 2001, pp. 54-56.
Granetzny, A., et al., "Pharmacologic heart rate reduction: effect of a novel specific bradyardic agent on the heart," The Thoracic and Cardiovascular Surgeon, vol. 46, 1998, pp. 63-69.
Lijnen, P. and Petrov, V: Renin-Angiotensin System, Hpertrophy and Gene Expression in Cardiac Myocytes; J. Mol Cell Cardiol, 31, pp. 949-970 (1999).
Stark, M., et al. Method for Improving Diagnostic Quality in Echocardiography; U.S. Appl. No. 11/470,303, filed Sep. 6, 2006.
U.S. Appl. No. 11/273,221, filed Nov. 14, 2005, first Inventor Brian Guth.
Gregor, P., et al.: Use of Verapamil In the Treatment of Hypertrophic Cardiomyopathy, Cor Et Vasa, vol. 28, No. 6, 1986, pp. 404-412.
Hartmann, A. et al: Persisting effect of Calcium-channel blockers on the left ventricular function in hypertrophic cardiomyopathy after 14 years' treatment, Anglology, vol. 47, No. 8, 1996 pp. 765-773.
Kober, G., et al: Clinical cardiology hypertrophic cardiomyopathy, Long-term verapamil versus propranolol treatment of hypertrophic cardiomyopathy in matched pairs of patients. Circulation Supplement, Abstracts from the 60th Scientific Session vol. 76, No. 4, 1987 p. IV-248.
Goodman & Gilman's: The Pharmacological Basis of Therapeutics, 10th Edition, McGraw-Hill Medical Publishing Division, 2001, pp. 54-56.
Epstein, S.E., et al; Verapamil: Its potential for causing serious complications in pateients with hypertrophic cardiomyopathy; Circulation, 1981; 64, pp. 437-441.
Database WPI, Section PQ. Week 199747 Derwent Publications Ltd. London, GB; Class P31; AN 1997-510672KOVTUN, et al: Determination of clinical efficiency of drugs used to treat hypertrophic cardiomyopathy using coefficient based on speed of movement of mitral valve, reflecting diastolic function of left ventricie, and stroke volume left auricle.
The Extra Pharmacopoeia, 30th Edition, The Pharmaceutical Press, London p. 668.
Nicholls, D.P., et al; Cardio Vascular effects of Alinidine and Propranolol alone and in combination with Hydralazine In Norman Man, Br. J. Clin. Pharmacol, (1983) 15 (1), 21-29.

* cited by examiner

USE OF BRADYCARDIAC SUBSTANCES IN THE TREATMENT OF MYOCARDIAL DISEASES ASSOCIATED WITH HYPERTROPHY AND NOVEL MEDICAMENT COMBINATIONS

RELATED APPLICATION DATA

This application is a 35 USC 371 case of PCT/EP01/04034 which claims priority to German application 100 18 401.4 filed Apr. 13, 2000.

Elevated heart rate may be treated with bradycardiac substances, particularly $Ca^{++}$ channel blockers such as diltiazem and verapamil or beta-receptor blockers such as atenolol, bisoprolol, carvedolol, metoprolol or propanolol and $i_f$ channel blockers such as zatebradine [1-(7,8-dimethoxy-1,3,4,5-tetrahydro-2H-3-benzazepin-2-on-3-yl)-3-[N-methyl-N-(2-(3,4-dimethoxy-phenyl)-ethyl)-propane] (see EP-B-0 065 229), 3-[(N-(2-(3,4-dimethoxy-phenyl)-ethyl)-piperidin-3-yl)-methyl]-(7,8-dimethoxy-1,3,4,5-tetrahydro-2H-3-benzazepin-2-one (see EP-B-0 224 794) and its enantiomers cilobradine [(+)-3-[(N-(2-(3,4-dimethoxy-phenyl)-ethyl)-piperidin-3-(S)-yl)-methyl]-(7,8-dimethoxy-1,3,4,5-tetrahydro-2H-3-benzazepin-2-one] or alinidine [2-(N-allyl-2,6-dichloro-anilino)-2-imidazolidine), cf. also U.S. Pat. No. 3,708,485], while zatebradine is also known to have a favourable activity in the treatment of cardiac insufficiency (see EP-B-0 471 388).

Moreover it is known that bradycardiac substances, particularly the abovementioned compounds, of which the $i_f$ channel blockers such as zatebradine, cilobradine or alinidine, and in particular cilobradine, are preferred, can have a beneficial effect on the symptoms of myocardial diseases accompanied by hypertrophy, particularly for the treatment of idiopathic hypertrophic cardiomyopathies (HCM) such as hypertrophy of the remainder of the myocardium after myocardial infarction, ischaemic cardiomyopathy, hypertrophy of the myocardium in valve defects and myocarditis under toxic or iatrogenic influences.

Surprisingly it has now been found that bradycardiac substances, of which the $i_f$ channel blockers such as zatebradine, cilobradine or alinidine, and in particular cilobradine, are preferred, not only have a favourable effect on the clinical symptoms of hypertrophic cardiomyopathy, but will even induce regression of these serious heart diseases.

The present invention thus relates to the new use of bradycardiac substances, particularly the abovementioned compounds, of which the $i_f$ channel blockers such as zatebradine, cilobradine or alinidine, and in particular cilobradine, are preferred, to induce the regression of myocardial diseases accompanied by hypertrophy, particularly for the treatment of idiopathic hypertrophic cardiomyopathies (HCM) in humans and domestic pets.

In order to achieve the effect according to the invention it is expedient to use the dosage known from the literature for the treatment of elevated heart rate for the individual bradycardiac substances. For example the single dose for cilobradine is 0.1 to 0.5 mg/kg per os, preferably 0.2 to 0.4 mg/kg, 1 to 3× daily, for zatebradine it is 0.2 to 1 mg/kg 2× daily and for alinidine it is 0.5 to 5 mg/kg 2× daily.

The new use of the bradycardiac substances according to the invention was investigated with the $i_f$ channel blocker cilobradine by way of example, using the following method:

A cat with severe hypertrophic cardiomyopathy (heart rate about 200 beats/minute), ECG with ST accentuations as a sign of myocardial ischaemia, increased creatinine kinase activity in the plasma and in the ultrasound image, massive compression of the ventricular wall with a reduction in the ventricular volume and the ejection fraction, exhibited a significant improvement in clinical symptoms after treatment with the $i_f$ channel blocker cilobradine (0.3 mg/kg per os, 2× daily) (relief from pain, normal ECG, return of normal physiological activity pattern).

Follow-up investigations after one year and after about 2 years' treatment surprisingly showed a regression in myocardial hypertrophy while the improvement in symptoms was maintained.

The hypertrophic cardiomyopathy in the cat serves as a model for the corresponding disease in humans (Kittleson et al., Circulation 91, 3172–3180 (1999)).

Treatment with the $i_f$ channel blocker cilobradine thus leads not only to an improvement in symptoms but also to regression of the disease.

The present invention also relates to drug combinations, containing at least one bradycardiac substance, particularly one of the abovementioned compounds, preferably an $i_f$ channel blocker, and at least one cardioactive substance such as a cardioglycoside, e.g. methyldigoxin or digitoxin, a vasodilator, e.g. nitroglycerine, an ACE inhibitor, e.g. captopril or enalapril, an angiotensin-II antagonist, e.g. losartan or telmisartan, which are also suitable for treating myocardial diseases accompanied by hypertrophy, particularly for the treatment of idiopathic hypertrophic cardiomyopathies (HCM), if a rise in heart rate can be prevented by combining them with a bradycardiac substance.

To achieve the effect according to the invention it is convenient to use the dosages known from the literature for the individual bradycardiac substances for the treatment of elevated heart rate and the dosages known from the literature for the cardioactive compound used.

For this purpose the bradycardiac substances, either on their own or combined with other cardioactive compounds, are formulated with one or more conventional inert carriers and/or diluents, e.g. with maize starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearyl alcohol, carboxymethylcellulose or fatty substances such as hard fat or suitable mixtures thereof, to produce conventional Galenic preparations such as plain or coated tablets, capsules, powders, suspensions, solutions, sprays or suppositories.

Thus, for example, the combination consisting of cilobradine and a cardioactive compound conveniently contains 0.1 to 0.5 mg/kg, preferably 0.2 to 0.4 mg/kg of cilobradine per os plus 0.01 to 1 mg of methyldigoxin, 1 to 2× daily, 0.01 to 1 mg of digoxin, 1× daily, 0.1 to 2 mg of nitroglycerine, 2 to 3× daily, 10 to 100 mg of captopril, 1 to 2× daily, 2 to 20 mg of enalapril, 1× daily, 10 to 200 mg of losartan, 2× daily, or 20 to 80 mg of telmisartan, 1× daily.

As the partners for the $i_f$ channel blockers in the drug combination additionally act on an independent biological system and $i_f$ channel blockers inhibit reflex increases in heart rate, which may occur in connection with the above combination partner, these have a synergistic activity.

The Examples that follow are intended to illustrate the invention without restricting it:

EXAMPLE 1

Capsules containing 1.25 mg of cilobradine

Composition:
1 capsule contains:

| | |
|---|---|
| lactose monohydrate | 82.75 mg |
| maize starch | 55.3 mg |

Method of Preparation

The active substance, lactose monohydrate and maize starch are mixed and packed into size 4 capsules.

EXAMPLE 2

Capsules containing 10 mg of cilobradine

Composition:
1 capsule contains:

| | |
|---|---|
| lactose monohydrate | 77.6 mg |
| maize starch | 51.7 mg |

Method of Preparation

The active substance, lactose monohydrate and maize starch are mixed and packed into size 4 capsules.

EXAMPLE 3

Tablets containing 7.5 mg of cilobradine

Composition:
1 tablet contains:

| | |
|---|---|
| active substance | 7.5 mg |
| maize starch | 59.5 mg |
| lactose | 48.0 mg |
| polyvinylpyrrolidone | 4.0 mg |
| magnesium stearate | 1.0 mg |
| | 120.0 mg |

Method of Preparation

The active substance, maize starch, lactose and polyvinylpyrrolidone are mixed and moistened with water. The moist mixture is forced through a sieve with a 1.5 mm mesh and dried at 45° C. The dry granules are passed through a sieve with a 1.0 mm mesh and mixed with magnesium stearate. The finished mixture is compressed in a tablet press with punches 7 mm in diameter provided with a dividing notch, to form tablets.

Weight of tablet: 120 mg

EXAMPLE 4

Coated tablets containing 5 mg of cilobradine 1 tablet core contains:

| | |
|---|---|
| active substance | 5.0 mg |
| maize starch | 41.5 mg |
| lactose | 30.0 mg |
| polyvinylpyrrolidone | 3.0 mg |
| magnesium stearate | 0.5 mg |
| | 80.0 mg |

Method of Preparation

The active substance, maize starch, lactose and polyvinylpyrrolidone are mixed thoroughly and moistened with water. The moist mass is forced through a sieve with a 1.0 mm mesh and dried at 45° C., then the granules are passed through the same sieve. After mixing with magnesium stearate, convex tablet cores with a diameter of 6 mm are compressed in a tablet-making machine. The tablet cores thus produced are coated in known manner with a coated consisting essentially of sugar and talc. The finished coated tablets are polished with wax.

Weight of coated tablet: 130 mg

EXAMPLE 5

Ampoules containing 5 mg of cilobradine 1 ampoule contains:

| | |
|---|---|
| active substance | 5.0 mg |
| sorbitol | 50.0 mg |
| water for injections ad | 2.0 mg |

Method of Preparation

In a suitable mixing vessel the active substance is dissolved in water for injections and the solution is made isotonic with sorbitol.

After filtration through a diaphragm filter, the solution is transferred into purified and sterilised ampoules under $N_2$ and autoclaved for 20 minutes in a stream of water vapour.

EXAMPLE 6

Suppositories containing 10 mg of cilobradine 1 suppository contains:

| | |
|---|---|
| active substance | 0.010 g |
| hard fat (e.g. Witepsol H 19 and W 45) | 1.690 g |
| | 1.700 g |

Method of Preparation

The hard fat is melted. At 38° C. the ground active substance is homogeneously dispersed in the melt. This is cooled to 35° C. and poured into slightly chilled suppository moulds.

EXAMPLE 7

| Drops solution containing 10 mg of cilobradine | |
|---|---|
| 100 ml of solution contain: | |
| active substance | 0.2 g |
| hydroxyethylcellulose | 0.15 g |
| tartaric acid | 0.1 g |
| sorbitol solution, 70% dry matter | 30.0 g |
| glycerol | 10.0 g |
| benzoic acid | 0.15 g |
| dist. water | ad 100 ml |

Method of Preparation

The distilled water is heated to 70° C. The hydroxyethylcellulose, benzoic acid and tartaric acid are dissolved therein with stirring. The solution is cooled to ambient temperature and the glycerol and the sorbitol solution are added with stirring. At ambient temperature the active substance is added and the mixture is stirred to dissolve it completely. It is then evacuated with stirring to eliminate air from the syrup.

The invention claimed is:

1. A method of inducing a regression of myocardial hypertrophy, said method comprising administering to a patient in need thereof a pharmaceutically effective amount of a pharmaceutical composition comprising cilobradine.

* * * * *